United States Patent [19]

Miller et al.

[11] Patent Number: 5,691,462

[45] Date of Patent: Nov. 25, 1997

[54] STABILIZED VINYL ETHER COMPOSITION

[75] Inventors: Mark M. Miller, Ridgewood; James A. Dougherty, Pequannock; M. J. Rhonheimer, East Hanover, all of N.J.

[73] Assignee: ISP Investments Inc., Wilmington, Del.

[21] Appl. No.: 711,771

[22] Filed: Sep. 10, 1996

[51] Int. Cl.$^6$ .................................................. C07C 41/00
[52] U.S. Cl. .................................... 568/580; 568/581
[58] Field of Search ................................. 568/581, 580

[56] References Cited

U.S. PATENT DOCUMENTS 3,415,891 12/1968 Turumaru et al. .................. 260/611.5
4,737,314 4/1988 Yokoyama et al. ...................... 252/551
5,010,173 4/1991 O'Lenick Jr. et al. ................. 528/408

*Primary Examiner*—Samuel Barts
*Attorney, Agent, or Firm*—Marilyn J. Maue; Walter Katz; Joshua J. Ward

[57] ABSTRACT

This invention relates to a stabilized hydrocarbon vinyl ether or hydroxy substituted hydrocarbon vinyl ether containing between 3 and 20 carbon atoms which contains between about 0.005 and about 0.75 weight % of an alkali metal salt of a $C_1$ to $C_{14}$ hydrocarbon ester.

5 Claims, No Drawings

STABILIZED VINYL ETHER COMPOSITION

BACKGROUND OF THE INVENTION

The relatively low molecular weight vinyl ethers are well known monomers for homo- and co- polymerizations in the manufacture of useful products such as protective coatings, lacquers, paints and the like. These monomers are also frequently employed as modifiers for polymers, notably polystyrene, and as plasticizers for nitrocellulose products. Notwithstanding their many uses, a major disadvantage in the use of these valuable ethers is their lack of resistance to discoloration upon standing or upon mixture with certain strong bases such as potassium or sodium hydroxide. Additionally, the unsubstituted vinyl ethers can enter into a cationic polymerization resulting in hazardous "runaway" exothermic conditions. In the case of hydroxy substituted vinyl ethers, the OH group readily undergoes intermolecular reaction with labile hydrogen to form undesirable acetal by-products. The later reaction is illustrated by the following as it pertains to hydroxybutyl vinyl ether.

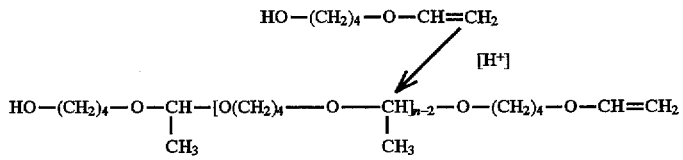

The above end to end reaction product inhibits further polymerization of the monomer and limits its usefulness.

Accordingly, it is an object of the present invention to overcome these disadvantages by stabilizing the vinyl ethers against the above reactions. Another object of the invention is to accomplish the desired stabilization without product degradation by an economically feasible and convenient method. These and other objects of the invention will become apparent from the following description and disclosure.

THE INVENTION

In accordance with the present invention there is provided a stabilized composition of a normally unstable $C_3$ to $C_{20}$ vinyl ether containing between about 0.005 and about 0.75 weight % of an alkali metal salt of a $C_1$ to $C_{14}$ unsubstituted ester.

The term "normally unstable vinyl ethers" is used throughout the specification to refer to unstabilized vinyl ethers which undergo discoloration upon standing or heating to an elevated temperature or which react exothermally in an uncontrolled preliminary manner or which enter into an intermemolecular reaction to form acetal products. Further, the unstable vinyl ethers of this invention are unsubstituted or hydroxy substituted vinyl ethers which are saturated aliphatic or are aromatically unsaturated ethers containing from one to three hydroxy groups. Suitable examples of these include cyclohexane dimethanol divinyl ethers and also vinyl methyl, vinyl ethyl, vinyl propyl, vinyl-1-hydroxypropyl, vinyl butyl, vinyl dodecyl, vinyl-1-hydroxybutyl, vinyl 1,3-dihydroxyhexyl, vinyl phenyl, vinyl hydroxyphenyl, vinyl trihydroxyphenyl ethers and mixtures thereof. Of these, the $C_2$ to $C_4$ aliphatic vinyl ethers optionally monosubstituted with a hydroxy radical are preferred.

The organic metal salt stabilizers of the composition include the formate, acetate, propionate, butyrate, phenate, phenylphenate metal salts and mixtures thereof. These salts are defined by the formula XOOY wherein X is an alkali metal, preferably K or Na, and Y is —C—COOR, saturated C—$C_1$ to $C_6$ alkyl, —CH or a monocyclic aromatic group. Of these stabilizers, Na and K acetates are preferred. Stabilization with the foregoing compounds inhibits the formation of color and premature reactions involving the vinyl ether monomers. Since the hydroxy substituted vinyl ethers encounter problems not at all related with those of the unsubstituted ethers, e.g. the formation of end to end oligomers, it is surprising the same stabilizing compounds are equally effective for stabilization of both species.

The present stabilization treatment involves the addition of between about 0.005 and about 0.75 weight %, preferably between about 0.008 and about 0.3 weight %, of the organic metal salt to the normally unstable vinyl ether under gentle agitation and ambient conditions including a slightly elevated temperature, e.g. up to 50° C. The resulting vinyl ether is stabilized against discoloration and undesirable side reactions under conditions of use.

Having thus generally described the invention, reference is now had to the accompanying examples which illustrate preferred embodiments but which are not to be construed as limiting to the scope of the invention as more broadly defined above and in the appended claims.

EXAMPLE 1

Five 100 gram aliquots of high purity 4-hydroxybutyl vinyl ether, HBVE, (RAPICURE HBVE), were weighed into 125 ml erlenmeyer flasks with magnetic stirrers. The flasks were labeled 1 through 5 and the following was added to each:

| Flask # | Stabilizer | Amount - grams | Wt. % |
|---------|------------|----------------|-------|
| 1 | No Addition | 0 | 0 |
| 2 | Potassium Acetate | 0.1 | 0.1 |
| 3 | Potassium Acetate | 0.01 | 0.01 |
| 4 | Sodium Acetate | 0.01 | 0.01 |
| 5 | Potassium Hydroxide | 0.01 | 0.01 |

The samples were then mixed for 10 minutes at ambient temperature until all traces of solids dissolved. The contents of each flask was divided into two equal portions in 2 ounce sealed sample jars. The samples were labelled A and B corresponding to the initial number designated 1-A, 1-B, 2-A, 2-B etc. The A samples were stored in a circulating air oven at 50° C. those marked A at ambient temperature (22°–25° C.) for 4.5 months. The samples were analyzed for various product degradation parameters after 18 weeks and the results are shown in following Table 1. As can be seen both of the samples 1-A and 1-B have formed cyclic (C-acetal) and linear acetals (L-acetal) and are no longer in commercial specification. All samples stabilized with potassium acetate or sodium acetate were stable for all specification parameters when compared to potassium hydroxide. Potassium hydroxide is known to cause problematic color instability not seen with the present noncaustic stabilizers. The acetate is also advantageous since it's solubility is 0.3% in HBVE.

TABLE 1

HBVE LONGTERM THERMAL STABILITY

| Samples | Time Elapsed | Color (APHA) | C-Acetal | L-Acetal | $B_1D^*$ | pH 10% Solution |
|---------|--------------|--------------|----------|----------|----------|------------------|
| 1-A | 18 weeks | 1.4 | 3.117 | 11.3186 | 1.094 | 6.33 |
| 1-B | 18 weeks | 1.4 | 0.5119 | 1.62 | 0.1018 | 5.98 |
| 2-A | 18 weeks | 1.4 | 0.0973 | 0.0419 | 0.0147 | 6.51 |
| 2-B | 18 weeks | 1.4 | 0.161 | 0.0201 | 0.0206 | 6.64 |
| 3-A | 18 weeks | 1.4 | 0.1283 | 0.0481 | 0.0285 | 6.86 |
| 3-B | 18 weeks | 1.4 | 0.2173 | 0.0218 | 0.0104 | 6.79 |
| 4-A | 18 weeks | 1.4 | 0.272 | 0.294 | 0.0056 | 7.04 |
| 4-B | 18 weeks | 1.4 | 0.177 | 0.0198 | 0.0057 | 6.95 |
| 5-A | 18 weeks | 2.7 | 0.1951 | 0.0174 | 0.0575 | 7.22 |
| 5-B | 18 weeks | 1.9 | 0.236 | 0.0135 | 0.0062 | 9.45 |

*butanediol

EXAMPLE 2

Twenty 5 grams of cyclohexyl vinyl ether (CVE) was placed in each of three 35 ml pressure tubes a, b and c. Stabilizers were added to the tubes as shown below in Table 2. Both KOH and potassium carbonate are insoluble in CVE, thus the stabilizer can be readily observed in the bottom of the tube.

TABLE 2

| Tube # | Stabilizer | Stabilizer Weight (gm) | Weight % Stabilizer |
|--------|------------|------------------------|---------------------|
| a | None | — | — |
| b | KOH | 0.025 | 0.1 |
| c | Potassium Carbonate | 0.025 | 0.1 |

Each tube was tightly capped and placed in a forced air oven at 50° C. and observed daily for purity, monomer color, and stabilizer appearance. Monomer purity and color remained constant, however, as shown below in Table 3, the KOH stabilizer rapidly discolors, turning dark brown within 2 days, while the potassium carbonate remains white.

TABLE 3

| # of days | Tube # Stabilizer | a none | b KOH | c $K_2CO_3$ |
|-----------|-------------------|--------|-------|-------------|
| 0 | Purity | 99.82 | 99.82 | 99.82 |
|   | APHA Color of CVE | 4.9 | 4.9 | 4.9 |
|   | Appearance of Stabilizer | — | white | white |
| 1 | Purity | 99.80 | 99.79 | 99.80 |
|   | APHA Color of CVE | 4.9 | 4.9 | 4.9 |
|   | Appearance of Stabilizer | — | yellow | yellow |
| 2 | Purity | 99.75 | 99.73 | 99.76 |
|   | APHA Color of CVE | 4.9 | 4.9 | 4.9 |
|   | Appearance of Stabilizer | — | brown | white |

EXAMPLE 3

Example 2 was repeated except the tubes d, e and f were stored under ambient conditions and were observed once a month. As shown in following Table 4 the KOH turned yellow within 3 months, while the potassium carbonate remained white.

TABLE 4

| # of days | Tube # Stabilizer | d none | e KOH | f $K_2CO_3$ |
|-----------|-------------------|--------|-------|-------------|
| 0 | Purity | 99.82 | 99.82 | 99.82 |
|   | APHA Color of CVE | 4.9 | 4.9 | 4.9 |
|   | Appearance of Stabilizer | — | white | white |
| 30 | Purity | 99.80 | 99.79 | 99.80 |
|   | APHA Color of CVE | 4.7 | 4.7 | 4.6 |
|   | Appearance of Stabilizer | — | white | white |
| 60 | Purity | 99.80 | 99.79 | 99.80 |
|   | APHA Color of CVE | 4.7 | 4.7 | 4.2 |
|   | Appearance of Stabilizer | — | slight yellow | white |
| 90 | Purity | 99.82 | 99.81 | 99.82 |
|   | APHA Color of CVE | 4.6 | 4.6 | 3.9 |
|   | Appearance of Stabilizer | — | yellow | white |

EXAMPLE 4

Example 3 was repeated except CVE was replaced with n-butyl vinyl ether (n-BVE) in tubes g, h and i. KOH and potassium carbonate are also insoluble in n-BVE. As shown in Table 5, the KOH stabilizer turned yellow within 1 month. The potassium carbonate stabilizer remained white for over three months.

TABLE 5

| # of days | Tube # Stabilizer | g none | h KOH | i $K_2CO_3$ |
|-----------|-------------------|--------|-------|-------------|
| 0 | Purity | 98.67 | 99.67 | 99.67 |
|   | APHA Color of CVE | 1.4 | 1.4 | 1.4 |
|   | Appearance of Stabilizer | — | white | white |
| 30 | Purity | 99.60 | 99.60 | 99.62 |
|   | APHA Color of CVE | 1.1 | 1.1 | 1.1 |
|   | Appearance of Stabilizer | — | brown | white |
| 60 | Purity | 99.52 | 99.79 | 99.80 |
|   | APHA Color of CVE | 0.8 | 1.0 | 0.8 |
|   | Appearance of Stabilizer | — | brown | white |
| 90 | Purity | 99.42 | 99.81 | 99.53 |
|   | APHA Color of CVE | 1.7 | 1.6 | 1.4 |
|   | Appearance of Stabilizer | — | brown | white |

What is claimed is:

1. A stabilized $C_3$ to $C_{20}$ hydrocarbon vinyl ether optionally substituted with 1–3 hydroxy radicals which contains between about 0.005 and about 0.75 weight of an alkali metal salt of a $C_1$ to $C_{14}$ saturated hydrocarbon ester.

2. The stabilized vinyl ether of claim 1 containing between about 0.008 and about 0.3 weight % of said alkali metal salt.

3. The stabilized vinyl ether of claim 1 or 2 wherein said metal salt is Na or K acetate.

4. The stabilized vinyl ether of claim 1 or 2 wherein said metal salt is Na or K carbonate.

5. The stabilized vinyl ether of claim 1 or 2 wherein said vinyl ether is a $C_4$ to $C_{12}$ aliphatic vinyl ether optionally monosubstituted with hydroxy.

* * * * *